US012577198B2

(12) United States Patent
Bolomey et al.

(10) Patent No.: US 12,577,198 B2
(45) Date of Patent: Mar. 17, 2026

(54) ACETONITRILE SEPARATION PROCESS

(71) Applicant: Ascend Performance Materials Operations LLC, Houston, TX (US)

(72) Inventors: Pascal Bolomey, Houston, TX (US); Kyle Kissell, Houston, TX (US); Basil Michaels, Houston, TX (US); Nick Sparkman, Houston, TX (US); Zhensheng Ding, Houston, TX (US)

(73) Assignee: Ascend Performance Materials Operations LLC, Houston, TX (US)

( * ) Notice: Subject to any disclaimer, the term of this patent is extended or adjusted under 35 U.S.C. 154(b) by 669 days.

(21) Appl. No.: 18/068,645

(22) Filed: Dec. 20, 2022

(65) Prior Publication Data

US 2023/0192600 A1     Jun. 22, 2023

Related U.S. Application Data

(60) Provisional application No. 63/291,765, filed on Dec. 20, 2021.

(51) Int. Cl.
*C07C 253/34*          (2006.01)
(52) U.S. Cl.
CPC .................................. *C07C 253/34* (2013.01)
(58) Field of Classification Search
CPC ...................................................... C07C 253/34
See application file for complete search history.

(56) References Cited

U.S. PATENT DOCUMENTS 4,308,108 A     12/1981  Higuchi et al.
4,362,603 A     12/1982  Presson et al.

6,780,289 B2     8/2004   Godbole
11,111,209 B2     9/2021   Michael et al.
2020/0157044 A1     5/2020   Michael et al.

FOREIGN PATENT DOCUMENTS

EP          0937707 B1     4/2003
GB          1 088 072 A    10/1967
WO      2002006212 A2      1/2002

OTHER PUBLICATIONS

International Application No. PCT/US2022/081996, International Search Report and Written Opinion, mailed on May 2, 2023, 12 pages.

*Primary Examiner* — Renee Robinson
(74) *Attorney, Agent, or Firm* — Womble Bond Dickinson (US) LLP

(57)                    ABSTRACT

A process for producing acetonitrile, the process comprising dehydrating a feedstock stream comprising acetonitrile, acrylonitrile, allyl alcohol, and water (and optionally methanol) in a dehydration (first) column to yield a dehydrated acetonitrile stream comprising acetonitrile and acrylonitrile, less than 1 wt % allyl alcohol, and less than 50 wt % water, and optionally hydrogen cyanide; distilling the dehydrated acetonitrile stream in a lights (second) column to yield a distillate stream comprising lights, and a bottoms stream comprising acetonitrile, acrylonitrile, water, and optionally hydrogen cyanide and acrylonitrile; extracting the distillation bottoms stream in an extraction (third) column to yield a raffinate stream comprising acetonitrile and less than 200 ppm acrylonitrile and an extract stream comprising water and acrylonitrile; purifying the raffinate stream to yield a product acetonitrile stream.

20 Claims, 1 Drawing Sheet

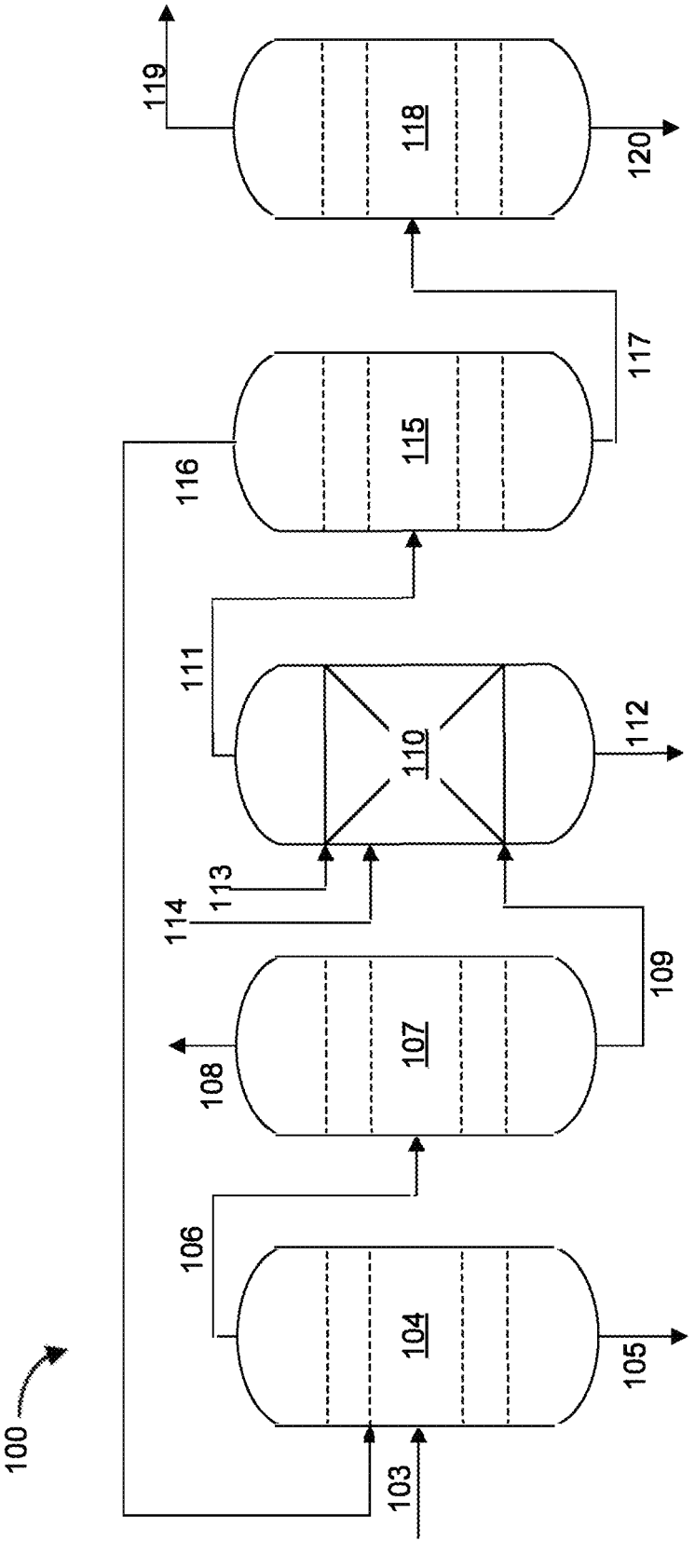

ACETONITRILE SEPARATION PROCESS

CROSS REFERENCE TO RELATED APPLICATION

This application claims priority to U.S. Provisional Application No. 63/291,765, filed on Dec. 20, 2021, which is incorporated herein by reference.

FIELD

The present disclosure relates generally to downstream separation processes having the ability to isolate acetonitrile, and which are particularly useful for the recovery of acetonitrile from industrial streams that include acrylonitrile, water, allyl alcohol, and oxazole, and optionally methanol.

BACKGROUND

Cyanocarbons, e.g., organic compounds having cyano functional groups, are known and are widely used in various applications. Many of these compounds, including acrylonitrile, are used as monomers to prepare various polymers, such as nylon, polyacrylonitrile, or acrylonitrile butadiene styrene. Several methods of producing cyanocarbons are known in the art, and these production methods often yield waste streams comprising small amounts of desirable co-products. For example, acetonitrile may be present in many of the conventional waste streams of industrial production processes. Typically, this co-product acetonitrile may be recovered using well-known separation schemes. These typical acrylonitrile process waste stream separation schemes, however, do not contemplate the presence of some other impurities in the waste streams, e.g., methanol, water, allyl alcohol, and/or oxazole, which can complicate acetonitrile isolation due to, e.g., impurities with similar physical properties as acetonitrile and the formation of an azeotrope with acetonitrile.

A number of processes for recovering acetonitrile are known in the art. For example, U.S. Pat. No. 4,362,603 discloses a process for recovering an acetonitrile byproduct from a stream comprising acetonitrile, water, hydrogen cyanide, acrylonitrile, and other organics such as oxazole, allyl alcohol, acetone, or propionitrile by distilling in three distillation zones at varying pressures.

As another example, U.S. Pat. No. 6,780,289 discloses a method for the purification of crude acetonitrile comprising distilling the crude acetonitrile in a first fractional distillation column at below atmospheric pressure, withdrawing a first side draw fraction comprising acetonitrile, distilling the first side draw fraction in a second fractional distillation column at super atmospheric pressure, and withdrawing from the second distillation a second side draw fraction comprising purified acetonitrile.

U.S. Pat. No. 11,111,209 discloses a process for producing a high-purity acetonitrile product from low-purity acetonitrile feedstock streams. In particular, this patent relates to a process for producing a sales-grade, high purity acetonitrile by (a) distilling the feedstock stream to yield a crude acetonitrile stream, (b) treating the crude acetonitrile stream to produce an intermediate acetonitrile stream, (c) purifying the intermediate acetonitrile stream in a pressure swing distillation system to produce a recycle stream and an acetonitrile product stream, (d) recycling the recycle stream to the first distillation column, and (e) distilling the acetonitrile product stream to yield a purified acetonitrile product stream of at least 98 wt % acetonitrile.

While these references may relate to acetonitrile separation, these references fail to contemplate the challenges of recovering acetonitrile from feedstock streams that comprise lesser amounts of acetonitrile, along with particular concentrations of, for example, acrylonitrile, methanol, water, allyl alcohol, hydrogen cyanide, and/or oxazole. Thus, the need exists for improved processes having more effective separation and/or recovery of by-product acetonitrile.

SUMMARY

The disclosure relates to a process for producing acetonitrile, the process comprising dehydrating, e.g., at a pressure less than 150 kPa, a feedstock stream comprising acetonitrile, acrylonitrile, allyl alcohol, and water (and optionally methanol and hydrogen cyanide), in a dehydration (first) column to yield a dehydrated acetonitrile stream comprising acetonitrile and acrylonitrile, less than 1 wt % allyl alcohol, and less than 50 wt % water, and optionally hydrogen cyanide, and optionally less than 20 wt % polymerized HCN and/or less than 25 wt % heavies, and optionally yielding a water stream comprising water, allyl alcohol, methanol, and heavies; distilling the dehydrated acetonitrile stream in a lights (second) column to yield a distillate stream comprising lights and optionally oxazole, methanol, and/or acrylonitrile, and a bottoms stream comprising acetonitrile, acrylonitrile, water, and optionally hydrogen cyanide and/or acrylonitrile and/or from 0.1 wt % to 20 wt % methanol, and/or acetonitrile-water azeotrope composition; (counter-currently) extracting the distillation bottoms stream in an extraction (third) column, optionally wherein an accelerator, e.g., methanol, is utilized during the extracting, to yield a raffinate stream comprising acetonitrile and less than 200 ppm, e.g., less than 50 ppm, acrylonitrile, e.g., less than 25 ppm, and optionally less than 200 ppm hydrogen cyanide and less than 50 wt % water, e.g., less than 25 wt % water, and optionally less than 1 wt % cyanide, and an extract stream comprising water and acrylonitrile; purifying the raffinate stream to yield a product acetonitrile stream. The purifying may comprise distilling the raffinate stream in a drying (fourth) column to yield an overhead comprising acetonitrile-water azeotrope and a bottoms stream comprising acetonitrile and low amounts of water and/or distilling the drying column bottoms in a product (fifth) column to yield a product stream comprising high purity acetonitrile. The process may further comprise recycling the drying column overhead to the dehydration column. The drying columns bottom may comprise propionitrile and less than 5 wt % water and wherein the distilling in the product column yields an overhead comprising greater than 95 wt % acetonitrile and a bottoms comprising propionitrile and optionally heavies.

BRIEF DESCRIPTION OF DRAWINGS

The present disclosure is described in detail below with reference to the appended drawings, wherein like numerals designate similar parts.

The FIGURE is a schematic illustration of a process for recovering acetonitrile in accordance with an embodiment.

DETAILED DESCRIPTION

As noted above, conventional acetonitrile purification schemes relate to the purification of acetonitrile feed streams that comprise lesser amounts of acetonitrile and no methanol.

It has been found that conventional acetonitrile separation processes are unable to effectively isolate acetonitrile from contaminating components that include for example acrylonitrile, methanol, water, oxazole, and allyl alcohol. One reason for this is that some components, such as methanol, can detrimentally create azeotropes during distillation steps. This azeotrope formation in conventional separation processes can lead to significant problems that include reduced separation efficiencies, poor final acetonitrile product purities, and lower acetonitrile product yields. Other impurities in the feedstock stream can, due to their chemical structures and physical properties, also complicate the isolation of acetonitrile from the feedstock at purities and/or yields necessary for certain downstream applications. In particular, separation of allyl alcohol and/or oxazole is difficult for a variety of reasons. The presence of acrylonitrile adds even more separation challenges.

Certain process streams, e.g., industrial waste/vent streams, have now been found to contain smaller, yet notable, amounts of acetonitrile. And, if done effectively, the isolation of this acetonitrile from these streams could advantageously results in significant quantities of high-purity acetonitrile product. To that end, it has now been discovered that by employing the specific separations schemes disclosed herein, purified acetonitrile can be effectively recovered from the aforementioned lower concentration process streams.

In particular, the use of, inter alia, a combined extraction/caustic treatment step has been found to be particularly effective in removing, inter alia, acrylonitrile and hydrogen cyanide by-products. It is postulated that these by-products may beneficially react with caustic to form lower volatility compounds, which in turn facilitates more efficient separation from the acetonitrile. In some cases, acrylonitrile content may be reduced to very low levels, e.g., less than 200 ppm. It has been further found that this low-acrylonitrile content (raffinate) stream, is much more easily processed by subsequent units, which provides for notable separation efficiency improvements, e.g. acrylonitrile content reduction to the ppb level.

In addition, the inventors have found that various components, e.g., methanol, concentration in various process streams, e.g., the feed stream to the extraction column, when kept at specific concentrations, e.g., from 0.1 wt % to 20 wt %, or from 1 wt % to 5 wt %, acts as an accelerator. Without being bound by theory, it is postulated that the accelerators enable the mass transfer of acrylonitrile from the acetonitrile, e.g., in the organic phase, into the caustic phase, which provides for additional separation efficiency benefits.

Beneficially, any negative effects related to the reaction and extraction cost are more than outweighed by benefits related to resulting increases in, e.g., the purity and/or yield of the final isolated acetonitrile product. Notably, the importance of the combination the extraction step, the caustic treatment, the methanol acceleration, and the other separation scheme unit operations/process parameters disclosed herein had not been previously appreciated.

Processes

The disclosure relates to a process for producing acetonitrile comprising the step of dehydrating a specific feedstock stream comprising acetonitrile and acrylonitrile and, optionally methanol, allyl alcohol, and water in a dehydration (first) column to yield a dehydrated acetonitrile stream. The dehydrated acetonitrile stream comprises acetonitrile and acrylonitrile, less than 1 wt % allyl alcohol, and less than 50 wt % water, and optionally hydrogen cyanide. The process further comprises the step of distilling the dehydrated acetonitrile stream in a lights (second) column to yield a distillate stream comprising lights and a bottoms stream comprising acetonitrile, acrylonitrile, water, and optionally hydrogen cyanide and acrylonitrile. As noted above, the process employs an extraction step in which the distillation bottoms stream is extracted in an extraction (third) column, along with a caustic treatment, to yield a raffinate stream comprising acetonitrile and low amounts, or acrylonitrile, e.g., less than 200 ppm or less than 25 ppm), and an extract stream comprising (dilute caustic) water and acrylonitrile (and other co-product/impurities such as hydroxypropionitrile). The raffinate may be purified to yield a product acetonitrile stream. Each of these steps/parameters will be discussed in more detail below.

The disclosed processes, in some cases, are conducted without the need for (hydrogen cyanide/acrylonitrile) digestion steps, which advantageously eliminates process complication and reduces capital expenditure.

Feedstock Stream

The feedstock stream of the provided separation process includes, inter alia, acetonitrile, methanol, acrylonitrile, allyl alcohol, hydrogen cyanide, oxazole, and water. The feedstock stream can include one or more waste streams from other industrial chemical processes, e.g., the production of acrylonitrile, allyl cyanide, butyronitrile, polyacrylonitrile, polyamides, polyaramids, or combinations thereof. In some cases, the feedstock stream may result from the treatment of an intermediate stream in a digester to remove hydrogen cyanide, thus yielding the feedstock stream. For example, waste streams from multiple processes for producing organic nitriles or derivatives thereof can be combined (and optionally treated) to form the feedstock stream. In some embodiments, the feedstock stream includes one or more waste streams, e.g., purge streams, from an acrylonitrile production process. In conventional acrylonitrile production processes, acetonitrile-containing waste streams are burned in waste heat boilers to suppress the formation of nitrogen oxides. This solution, however, fails to capture the by-product acetonitrile. In the processes disclosed herein, however, these waste streams can be processed to recover the acetonitrile, preferably in at a high purity level.

In some embodiments, the concentration of acetonitrile in the feedstock stream ranges from 1 wt % to 50 wt %, e.g., from 1 wt % to 40 wt %, from 2 wt % to 35 wt %, from 3 wt % to 30 wt %, from 5 wt % to 25 wt %, from 10 wt % to 20 wt %, or from 12 wt % to 20 wt %. In terms of upper limits, the acetonitrile concentration in the feedstock stream can be less than 50 wt %, e.g., less than 40 wt %, less than 35 wt %, less than 30 wt %, less than 25 wt %, less than 20 wt %, less than 18 wt %, or less than 16 wt %. In terms of lower limits, the acetonitrile concentration in the feedstock stream can be greater than 1 wt %, e.g., greater than 2 wt %, greater than 3 w %, greater than 4 wt %, greater than 5 wt %, greater than 7 wt %, greater than 10 wt %, greater than 12 wt %, greater than 14 wt %, or greater than 15 wt %. Generally, as used herein, the weight percentages are based on the total weight of the respective stream. For example, with respect to the feedstock stream, the weight percentages include all components of the feedstock stream.

In some embodiments, the feedstock stream further includes acrylonitrile. The concentration of acrylonitrile in the feedstock stream can range, for example, from 0.05 wt % to 5 wt %, e.g., from 0.07 wt % to 3.5 wt %, from 0.1 wt % to 2.5 wt %, from 0.1 wt % to 1.5 wt %, from 0.2 wt % to 1.2 wt %, or from 0.25 wt % to 0.75 wt %. In terms of upper limits, the acrylonitrile concentration in the feedstock stream can be less than 5 wt %, e.g., less than 3.5 wt %, less than 2.5 wt %, less than 1.5 wt %, less than 1.2 wt %, less than 1 wt %, less than 0.75 wt %, or less than 0.5 wt %. In terms of lower limits, the acrylonitrile concentration in the feedstock stream can be greater than 0.05 wt %, e.g., greater than 0.07 wt %, greater than 0.1 wt %, greater than 0.15 wt %, greater than 0.2 wt %, greater than 0.25 wt %, or greater than 0.3 wt %.

In some embodiments, feedstock stream comprises allyl alcohol. The concentration of allyl alcohol may have ranges and limits as discussed above for acrylonitrile. The concentration of allyl alcohol in the feedstock stream can range, for example, from 0.05 wt % to 5 wt %, e.g., from 0.07 wt % to 3.5 wt %, from 0.1 wt % to 2.5 wt %, from 0.1 wt % to 1.5 wt %, from 0.2 wt % to 1.2 wt %, or from 0.25 wt % to 0.75 wt %. In terms of upper limits, the allyl alcohol concentration in the feedstock stream can be less than 5 wt %, e.g., less than 3.5 wt %, less than 2.5 wt %, less than 1.5 wt %, less than 1.2 wt %, less than 1 wt %, less than 0.75 wt %, or less than 0.5 wt %. In terms of lower limits, the allyl alcohol concentration in the feedstock stream can be greater than 0.05 wt %, e.g., greater than 0.07 wt %, greater than 0.1 wt %, greater than 0.15 wt %, greater than 0.2 wt %, greater than 0.25 wt %, or greater than 0.3 wt %.

In some embodiments, the concentration of water in the feedstock stream ranges from 40 wt % to 98 wt %, e.g., from 40 wt % to 95 wt %, from 45 wt % to 90 wt %, from 55 wt % to 85 wt %, from 60 wt % to 80 wt %, or from 65 wt % to 75 wt %. In terms of upper limits, the water concentration in the feedstock stream can be less than 98 wt %, e.g., less than 95 wt %, less than 90 wt %, less than 85 wt %, less than 80 wt %, less than 75 wt %, or less than 72 wt %. In terms of lower limits, the water concentration in the feedstock stream can be greater than 40 wt %, e.g., greater than 45 wt %, greater than 50 wt %, greater than 55 wt %, greater than 60 wt %, greater than 65 wt %, or greater than 68 wt %.

In some embodiments, the feedstock comprises oxazole. The concentration of oxazole in the feedstock stream can range, for example, from 0.05 wt % to 5 wt %, e.g., from 0.07 wt % to 3.5 wt %, from 0.1 wt % to 2.5 wt %, from 0.1 wt % to 1.5 wt %, from 0.2 wt % to 1.2 wt %, or from 0.25 wt % to 1 wt %. In terms of upper limits, the oxazole concentration in the feedstock stream can be less than 5 wt %, e.g., less than 3.5 wt %, less than 2.5 wt %, less than 1.5 wt %, less than 1.2 wt %, less than 1 wt %, less than 0.75 wt %, or less than 0.5 wt %. In terms of lower limits, the oxazole concentration in the feedstock stream can be greater than 0.05 wt %, e.g., greater than 0.07 wt %, greater than 0.1 wt %, greater than 0.15 wt %, greater than 0.2 wt %, greater than 0.25 wt %, or greater than 0.3 wt %.

In some embodiments, the feedstock stream further includes hydrogen cyanide. The concentration of hydrogen cyanide may have the ranges and limits as discussed above for oxazole. The concentration of hydrogen cyanide in the feedstock stream can range, for example, from 0.05 wt % to 5 wt %, e.g., from 0.07 wt % to 3.5 wt %, from 0.1 wt % to 2.5 wt %, from 0.1 wt % to 1.5 wt %, from 0.2 wt % to 1.2 wt %, or from 0.25 wt % to 1 wt %. In terms of upper limits, the hydrogen cyanide concentration in the feedstock stream can be less than 5 wt %, e.g., less than 3.5 wt %, less than 2.5 wt %, less than 1.5 wt %, less than 1.2 wt %, less than 1 wt %, less than 0.75 wt %, or less than 0.5 wt %. In terms of lower limits, the hydrogen cyanide concentration in the feedstock stream can be greater than 0.05 wt %, e.g., greater than 0.07 wt %, greater than 0.1 wt %, greater than 0.15 wt %, greater than 0.2 wt %, greater than 0.25 wt %, or greater than 0.3 wt %.

In some embodiments, the feedstock stream further includes methanol. In some cases the methanol is present in specific amounts. As a result, separation complications become more prevalent, e.g., in view of methanol-containing azeotrope formation. The concentration of methanol in the feedstock stream can range, for example, from 0.1 wt % to 20 wt %, e.g., from 0.5 wt % to 15 wt %, from 1 wt % to 15 wt %, from 1 wt % to 10 wt %, from 2 wt % to 8 wt %, or from 3 wt % to 7 wt %. In terms of upper limits, the methanol concentration in the feedstock stream can be less than 20 wt %, e.g., less than 15 wt %, less than 12 wt %, less than 10 wt %, less than 9 wt %, less than 8 wt %, less than 7 wt %, or less than 6 wt %. In terms of lower limits, the methanol concentration in the feedstock stream can be greater than 0.1 wt %, e.g., greater than 0.2 wt %, greater than 0.5 wt %, greater than 0.7 wt %, greater than 1 wt %, greater than 1.5 wt %, greater than 2 wt %, greater than 2.5 wt %, greater than 3 wt %, or greater than 3.5 wt %.

In some embodiments, the feedstock stream further includes propionitrile. The concentration of propionitrile may have the concentration ranges and limits as discussed above for allyl alcohol and/or acrylonitrile. The concentration of propionitrile in the feedstock stream can range, for example, from 0.05 wt % to 5 wt %, e.g., from 0.07 wt % to 3.5 wt %, from 0.1 wt % to 2.5 wt %, from 0.1 wt % to 1.5 wt %, from 0.2 wt % to 1.2 wt %, or from 0.25 wt % to 0.75 wt %. In terms of upper limits, the propionitrile concentration in the feedstock stream can be less than 5 wt %, e.g., less than 3.5 wt %, less than 2.5 wt %, less than 1.5 wt %, less than 1.2 wt %, less than 1 wt %, less than 0.75 wt %, or less than 0.5 wt %. In terms of lower limits, the propionitrile concentration in the feedstock stream can be greater than 0.05 wt %, e.g., greater than 0.07 wt %, greater than 0.1 wt %, greater than 0.15 wt %, greater than 0.2 wt %, greater than 0.25 wt %, or greater than 0.3 wt %.

In some embodiments, the feedstock stream further includes acetone. The concentration of acetone in the feedstock stream can range from 0.008 wt % to 0.2 wt %, e.g., from 0.008 wt % to 0.055 wt %, from 0.011 wt % to 0.076 wt %, from 0.015 wt % to 0.11 wt %, from 0.021 wt % to 0.14 wt %, or from 0.029 wt % to 0.2 wt %. In terms of upper limits, the acetone concentration in feedstock stream can be less than 0.2 wt %, e.g., less than 0.14 wt %, less than 0.11 wt %, less than 0.076 wt %, less than 0.055 wt %, less than 0.04 wt %, less than 0.029 wt %, less than 0.021 wt %, less than 0.015 wt %, or less than 0.011 wt %. In terms of lower limits, the acetone concentration in the feedstock stream can be greater than 0.008 wt %, e.g., greater than 0.011 wt %, greater than 0.015 wt %, greater than 0.021 wt %, greater than 0.029 wt %, greater than 0.04 wt %, greater than 0.055 wt %, greater than 0.076 wt %, greater than 0.11 wt %, or greater than 0.14 wt %.

In some embodiments, the feedstock stream further includes one or more other impurities, typically in small concentrations, e.g., ppm or ppb. These impurities can include, for example, various waste products that result from the production of organic nitriles and derivatives thereof. For example, the feedstock stream can include one or more acrylamides, azoles, aliphatic nitriles, aromatic nitriles, alcohols, aldehydes, acrolein, fumarin, cyanide salts, derivatives thereof, or a combination thereof.

Dehydration (Water)

The process comprises the step of dehydrating the feedstock stream, e.g., in a dehydration (first) column or combination of columns, to yield a dehydrated acetonitrile stream. The dehydrated acetonitrile stream comprises acetonitrile and acrylonitrile, less than 1 wt % allyl alcohol, and less than 50 wt % water, and optionally hydrogen cyanide and azeotrope compositions, e.g., ACN/water azeotrope compositions. A dehydration (aqueous) bottoms stream comprising a high concentration of water along with heavies, e.g., allyl alcohol, is also formed. It is recycled elsewhere in the process, e.g., to quench columns, where it may advantageously serve as make-up water in the quench operation. Because of the specific separation and the resultant content of the bottoms stream, unexpected process efficiencies are achieved. Beneficially, the distillation is operated such that most, if not all, of the allyl alcohol is removed, which advantageously contributes to downstream efficiencies. Without the specific purification, the bottoms stream would not be suitable for such purposes.

The structure of the dehydration distillation column(s) can vary widely according to designs known to those of ordinary skill in the art, and any suitable column can be employed as long as the separation specifications described herein are achieved. For example the dehydration distillation column can include any suitable separation device or combination of separation devices. The dehydration distillation column can include a column, e.g., a standard distillation column, an extractive distillation column and/or an azeotropic distillation column. In some cases, the term "dehydration distillation column" refers to multiple distillation columns configured to operate in conjunction with one another.

The dehydration step generally (and the dehydration distillation column in particular) may be configured and operated such that the concentration of water in the dehydration distillate stream is less than that in the feedstock stream. It can be beneficial for the provided separation process to remove much of the water of the intermediate acetonitrile stream in the first distillation, rather than in later unit operations to realize energy and cost efficiencies and/or to provide a final product acetonitrile stream having a higher acetonitrile product purity.

The feedstock stream of the provided separation process is dehydrated to remove a significant portion of the water from the feedstock stream, producing a dehydrated acetonitrile stream. As noted above, a low concentration of water in the dehydrated stream improves the efficiency of the downstream operations. This then results in improved purities and yields for the final product acetonitrile stream. The dehydration step may be handled in many ways, as long as enough water removal is achieved, e.g., as long as a dehydrated stream having a suitably low water content is produced. In some cases, a single dehydration unit may be employed. In other cases, multiple units may be used to achieve the dehydration.

In some embodiments, the concentration of acetonitrile in the dehydrated acetonitrile stream ranges from 25 wt % to 95 wt %, e.g., from 30 wt % to 90 wt %, from 40 wt % to 85 wt %, from 50 wt % to 85 wt %, from 60 wt % to 85 wt %, or from 65 wt % to 85 wt %. In terms of upper limits, the acetonitrile concentration in the dehydrated acetonitrile stream can be less than 95 wt %. e.g., less than 90 wt %, less than 85 wt %, less than 82 wt %, less than 80 wt %, or less than 78 wt %. In terms of lower limits, the acetonitrile concentration in the dehydrated acetonitrile stream can be greater than 25 wt %, e.g., greater than 30 wt %, greater than 40 wt %, greater than 50 wt %, greater than 60 wt %, greater than 70 wt %, greater than 72 wt %.

In some embodiments, the concentration of water in the dehydrated acetonitrile stream ranges from 0 wt % to 50 wt %, e.g., from 0 wt % to 25 wt %, from 1 wt % to 30 wt %, from 2 wt % to 25 wt %, from 5 wt % to 25 wt %, 5 wt % to 20 wt %, or from 10 wt % to 20 wt %. In terms of upper limits, the water concentration in the dehydrated acetonitrile stream can be less than 50 wt %, e.g., less than 40 wt %, less than 30 wt %, less than 25 wt %, less than 20 wt %, or less than 15 wt %. In terms of lower limits, the water concentration in the dehydrated acetonitrile stream can be greater than 0, e.g., greater than 0.1 wt %, greater than 1 wt %, greater than 2 wt %, greater than 5 wt %, greater than 10 wt %, or greater than 12 wt %.

In some embodiments, the concentration of water in the dehydration bottoms stream ranges from 70 wt % to 99 wt %, e.g., from 75 wt % to 99 wt %, from 80 wt % to 97 wt %, from 85 wt % to 96 wt %, from 88 wt % to 96 wt %, or from 90 wt % to 96 wt %. In terms of upper limits, the water concentration in the dehydration bottoms stream can be less than 99 wt %, e.g., less than 98 wt %, less than 97 wt %, less than 96 wt %, less than 95 wt %, or less than 92 wt %. In terms of lower limits, the water concentration in the dehydration bottoms stream can be greater than 70 wt %, e.g., greater than 75 wt %, greater than 80 wt %, greater than 85 wt %, greater than 88 wt %, or greater than 90 wt %.

In some embodiments, the mass ratio of the water in the dehydration bottoms stream to the water in the dehydration distillate stream ranges from 10:1 to 200:1, e.g., from 10:1 to 60:1, from 13:1 to 81:1, from 18:1 to 110:1, from 25:1 to 150:1, or from 33:1 to 200:1. In terms of upper limits, the mass ratio of water in the dehydration bottoms stream to the dehydration distillate stream can be less than 200:1, e.g., less than 150:1, less than 110:1, less than 81:1, less than 60:1, less than 45:1, less than 33:1, less than 25:1, less than 18:1, or less than 13:1. In terms of lower limits, the mass ratio of water in the dehydration bottoms stream to the dehydration distillate stream can be greater than 10:1, e.g., greater than 13:1, greater than 18:1, greater than 25:1, greater than 33:1, greater than 45:1, greater than 60:1, greater than 81:1, greater than 110:1, or greater than 150:1.

In some embodiments, the concentration of allyl alcohol in the dehydrated acetonitrile stream ranges from 0 wt % to 3.5 wt %, e.g., from 0 wt % to 2 wt %, from 0.01 wt % to 1.5 wt %, or from 0.01 wt % to 0.5 wt %. In terms of upper limits, the allyl alcohol concentration in the dehydrated acetonitrile stream can be less than 3.5 wt %, e.g., less than 2 wt %, less than 1.5 wt %, less than 1 wt %, less than 0.7 wt %, less than 0.5 wt %, less than 0.3 wt %, or less than 0.2 wt %. In terms of lower limits, the allyl alcohol concentration in the dehydrated acetonitrile stream can be greater than 0 wt %, e.g., greater than 0.01 wt %, greater than 0.02 wt %, greater than 0.05 wt %, or greater than 0.1 wt %. In some cases, the dehydrated acetonitrile stream comprises little or even no allyl alcohol. Beneficially, the distillation is operated such that most, if not all, of the allyl alcohol is removed, which advantageously contributes to downstream efficiencies.

In some embodiments, the concentration of allyl alcohol in the dehydration bottoms stream ranges from 0 wt % to 3 wt %, e.g., from 0 wt % to 1.5 wt %, from 0.01 wt % to 1 wt %, from 0.05 wt % to 1 wt %, from 0.1 wt % to 0.5 wt %, or from 0.1 wt % to 0.4 wt %. In terms of upper limits, the allyl alcohol concentration in the dehydration bottoms stream can be less than 3 wt %, e.g., less than 1.5 wt %, less than 1 wt %, less than 0.5 wt %, or less than 0.4 wt %. In terms of lower limits, the allyl alcohol concentration in the dehydration bottoms stream can be greater than 0 wt %, e.g., greater than 0.01 wt %, greater than 0.05 wt %, greater than 0.1 wt %, or greater than 0.2 wt %.

In some embodiments, the concentration of methanol in the dehydrated acetonitrile stream ranges from 0 wt % to 20 wt %, e.g., from 0.1 wt % to 15 wt %, from 0.5 wt % to 10 wt %, or from 1 wt % to 5 wt %. In terms of upper limits, the methanol concentration in the dehydrated acetonitrile stream can be less than 20 wt %, e.g., less than 15 wt %, less than 10 wt %, less than 8 wt %, less than 5 wt %, less than 3 wt %, or less than 2 wt %. In terms of lower limits, the methanol concentration in the dehydrated acetonitrile stream can be greater than 0 wt %, e.g., greater than 0.1 wt %, greater than 0.5 wt %, greater than 0.8 wt %, or greater than 1 wt %.

In some embodiments, the concentration of methanol in the dehydration bottoms stream ranges from 0 wt % to 20 wt %, e.g., from 0.1 wt % to 15 wt %, from 0.5 wt % to 10 wt %, from 1 wt % to 8 wt %, or from 2 wt % to 6 wt %. In terms of upper limits, the methanol concentration in the dehydration bottoms stream can be less than 20 wt %, e.g., less than 15 wt %, less than 10 wt %, less than 8 wt %, or less than 6 wt %. In terms of lower limits, the methanol concentration in the dehydration bottoms stream can be greater than 0 wt %, e.g., greater than 0.1 wt %, greater than 0.5 wt %, greater than 1 wt %, or greater than 2 wt %.

In some embodiments, the concentration of acrylonitrile in the dehydrated acetonitrile stream ranges from 0 wt % to 10 wt %, e.g., from 0.01 wt % to 9 wt %, from 0.05 wt % to 6 wt %, from 0.1 wt % to 5 wt %, or from 0.2 wt % to 3 wt %. In terms of upper limits, the acrylonitrile concentration in the dehydrated acetonitrile stream can be less than 10 wt %, e.g., less than 9 wt %, less than 6 wt %, less than 5 wt %, less than 3 wt %, less than 2 wt %, or less than 1 wt %. In terms of lower limits, the acrylonitrile concentration in the dehydrated acetonitrile stream can be greater than 0 wt %, e.g., greater than 0.01 wt %, greater than 0.05 wt %, greater than 0.1 wt %, or greater than 0.5 wt %.

In some embodiments, the dehydrated acetonitrile stream further includes oxazole. The concentration of oxazole in the dehydrated acetonitrile stream may be as discussed above for the concentration of methanol in the dehydrated acetonitrile stream.

In some embodiments, the concentration of heavies in the dehydration bottoms stream ranges from 0 wt % to 20 wt %, e.g., from 0.1 wt % to 15 wt %, from 0.5 wt % to 10 wt %, from 1 wt % to 8 wt %, or from 2 wt % to 6 wt %. In terms of upper limits, the methanol concentration in the dehydration bottoms stream can be less than 20 wt %, e.g., less than 15 wt %, less than 10 wt %, less than 8 wt %, or less than 6 wt %. In terms of lower limits, the methanol concentration in the dehydration bottoms stream can be greater than 0 wt %, e.g., greater than 0.1 wt %, greater than 0.5 wt %, greater than 1 wt %, or greater than 2 wt %.

In some embodiments, the dehydration distillation column is operated at a pressure ranging from 0.5 kPa to 150 kPa, e.g., from 1 kPa to 125 kPa, from 10 kPa to 100 kPa, from 25 kPa to 100 kPa, or from 25 kPa to 75 kPa. In terms of upper limits, the dehydration distillation column operating pressure can be less than 150 kPa, e.g., less than 125 kPa, less than 100 kPa, less than 75 kPa, less than 50 kPa, or less than 35 kPa. In terms of lower limits, the removal column distillation column operating pressure can be greater than 0.5 kPa, e.g., greater than 1 kPa, greater than 5 kPa, greater than 10 kPa, greater than 20 kPa, or greater than 25 kPa. Operation at these pressures, in some cases, provides for the aforementioned benefits.

The distillation, e.g., the first column(s), operates under lower pressure, e.g., under vacuum pressure (less than 100 kPa, less than 75 kPa, less than 50 kPa, or less than 40 kPa) to improve the separation. The use of a vacuum column as a first column has been found to reduce hydrogen cyanide polymerization in the first column. The reduction in polymerized hydrogen cyanide provides for reduced fouling of the upper portion of the column and overhead apparatus thus increasing the time the column can be used before removal of the polymerized HCN is required. This results in a superior acetonitrile product particularly because the resulting product has fewer components that absorb in the ultraviolet range. In addition, this may beneficially reduce the amount of water as early as possible in the purification process thereby reducing the amount of material to be recycled.

The amount of theoretical stages is advantageously kept low, e.g., less than 50 stages, less than 45 stages, less than 40 stages, or less than 39 stages.

In some embodiments, the concentration of polymerized HCN in the dehydration bottoms stream ranges from 0 wt % to 20 wt %, e.g., from 0.1 wt % to 15 wt %, from 0.5 wt % to 10 wt %, or from 1 wt % to 5 wt %. In terms of upper limits, the polymerized HCN concentration in the dehydration bottoms stream can be less than 20 wt %, e.g., less than 15 wt %, less than 10 wt %, less than 8 wt %, less than 5 wt %, less than 3 wt %, less than 2 wt %, or less than 1 wt %. In terms of lower limits, the polymerized HCN concentration in the dehydration bottoms stream can be greater than 0 wt %, e.g., greater than 0.1 wt %, greater than 0.5 wt %, greater than 0.8 wt %, or greater than 1 wt %.

In some cases, polymerized HCN may collect or remain on the surface of the column walls & internals).

Distillation (Lights)

The process further comprises the step of distilling the dehydrated acetonitrile stream in a lights (second) column to yield a distillate stream comprising lights and a bottoms stream comprising acetonitrile, acrylonitrile, water, and optionally hydrogen cyanide and acrylonitrile. The lights (second) distillation column(s) may separate many of the light organics, which can optionally be then directed to waste heat boiler(s).

In some embodiments, the concentration of acetonitrile in the bottoms stream ranges from 25 wt % to 95 wt %, e.g., from 30 wt % to 90 wt %, from 40 wt % to 85 wt %, from 50 wt % to 85 wt %, from 60 wt % to 85 wt %, or from 65 wt % to 85 wt %. In terms of upper limits, the acetonitrile concentration in the bottoms stream can be less than 95 wt %. e.g., less than 90 wt %, less than 85 wt %, less than 82 wt %, less than 80 wt %, or less than 78 wt %. In terms of lower limits, the acetonitrile concentration in the bottoms stream can be greater than 25 wt %, e.g., greater than 30 wt %, greater than 40 wt %, greater than 50 wt %, greater than 60 wt %, greater than 70 wt %, greater than 72 wt %.

In some cases, the acetonitrile may be present in the bottoms stream in the form of an acetonitrile azeotrope composition, e.g., and acetonitrile-water azeotrope (76.1° C.).

In some embodiments, the concentration of methanol in the bottoms stream ranges from 0 wt % to 3.5 wt %, e.g., from 0 wt % to 2 wt %, from 0.01 wt % to 1.5 wt %, or from 0.01 wt % to 0.5 wt %. In terms of upper limits, the methanol concentration in the bottoms stream can be less than 3.5 wt %, e.g., less than 2 wt %, less than 1.5 wt %, less than 1 wt %, less than 0.7 wt %, less than 0.5 wt %, less than 0.3 wt %, or less than 0.2 wt %. In terms of lower limits, the methanol concentration in the bottoms stream can be greater than 0 wt %, e.g., greater than 0.01 wt %, greater than 0.02 wt %, greater than 0.05 wt %, or greater than 0.1 wt %. In some cases, the dehydrated acetonitrile stream comprises little or even no methanol.

Hydrogen cyanide may be present in concentrations ranging from 0 wt % to 3.5 wt %, e.g., from 0 wt % to 2 wt %, from 0.01 wt % to 1.5 wt %, or from 0.01 wt % to 0.5 wt %. In terms of upper limits, the hydrogen cyanide concentration in the bottoms stream can be less than 3.5 wt %, e.g., less than 2 wt %, less than 1.5 wt %, less than 1 wt %, less than 0.7 wt %, less than 0.5 wt %, less than 0.3 wt %, or less than 0.2 wt %. In terms of lower limits, the hydrogen cyanide concentration in the bottoms stream can be greater than 0 wt %, e.g., greater than 0.01 wt %, greater than 0.02 wt %, greater than 0.05 wt %, or greater than 0.1 wt %.

In some embodiments, the concentration of oxazole in the bottoms stream can range, for example, from 0.05 wt % to 5 wt %, e.g., from 0.07 wt % to 3.5 wt %, from 0.1 wt % to 2.5 wt %, from 0.1 wt % to 1.5 wt %, from 0.2 wt % to 1.2 wt %, or from 0.25 wt % to 0.75 wt %. In terms of upper limits, the oxazole concentration in the bottoms stream can be less than 5 wt %, e.g., less than 3.5 wt %, less than 2.5 wt %, less than 1.5 wt %, less than 1.2 wt %, less than 1 wt %, less than 0.75 wt %, or less than 0.5 wt %. In terms of lower limits, the oxazole concentration in the bottoms stream can be greater than 0.05 wt %, e.g., greater than 0.07 wt %, greater than 0.1 wt %, greater than 0.15 wt %, greater than 0.2 wt %, greater than 0.25 wt %, or greater than 0.3 wt %.

In some embodiments, the concentration of acrylonitrile in the bottoms stream ranges from 0 wt % to 3.5 wt %, e.g., from 0 wt % to 2 wt %, from 0.01 wt % to 1.5 wt %, or from 0.01 wt % to 0.5 wt %. In terms of upper limits, the acrylonitrile concentration in the bottoms stream can be less than 3.5 wt %, e.g., less than 2 wt %, less than 1.5 wt %, less than 1 wt %, less than 0.7 wt %, less than 0.5 wt %, less than 0.3 wt %, less than 0.2 wt %, or less than 0.1. In terms of lower limits, the acrylonitrile concentration in the bottoms stream can be greater than 0 wt %, e.g., greater than 0.01 wt %, greater than 0.02 wt %, greater than 0.05 wt %, or greater than 0.1 wt %. In some cases, the bottoms stream comprises little or even no methanol.

In some embodiments, the concentration of acetonitrile in the lights distillate stream ranges from 1 wt % to 50 wt %, e.g., from 2 wt % to 40 wt %, from 5 wt % to 35 wt %, from 10 wt % to 30 wt %, or from 15 wt % to 25 wt %. In terms of upper limits, the acetonitrile concentration in the lights distillate stream can be less than 50 wt %, e.g., less than 40 wt %, less than 35 wt %, less than 30 wt %, or less than 25 wt %. In terms of lower limits, the acetonitrile concentration in the lights distillate stream can be greater than 1 wt %, e.g., greater than 2 wt %, greater than 5 wt %, greater than 10 wt %, or greater than 15 wt %. Similar concentrations for oxazole, methanol, and/or hydrogen cyanide in the lights distillate stream are also contemplated.

In some embodiments, the concentration of acrylonitrile in the lights distillate stream ranges from 1 wt % to 25 wt %, e.g., from 2 wt % to 20 wt %, from 5 wt % to 18 wt %, from 7 wt % to 15 wt %, or from 7 wt % to 12 wt %. In terms of upper limits, the acrylonitrile concentration in the lights distillate stream can be less than 25 wt %, e.g., less than 20 wt %, less than 18 wt %, less than 15 wt %, or less than 12 wt %. In terms of lower limits, the acrylonitrile concentration in the lights distillate stream can be greater than 1 wt %, e.g., greater than 2 wt %, greater than 5 wt %, greater than 7 wt %, or greater than 8 wt %.

In some embodiments, the concentration of acetone in the lights removal distillate stream ranges from 0.35 wt % to 8.5 wt %, e.g., from 0.35 wt % to 2.4 wt %, from 0.48 wt % to 3.3 wt %, from 0.66 wt % to 4.5 wt %, from 0.91 wt % to 6.2 wt %, or from 1.3 wt % to 8.5 wt %. In terms of upper limits, the acetone concentration in the lights removal distillate can be less than 8.5 wt %, e.g., less than 6.2 wt %, less than 4.5 wt %, less than 3.3 wt %, less than 2.4 wt %, less than 1.7 wt %, less than 1.3 wt %, less than 0.91 wt %, less than 0.66 wt %, or less than 0.48 wt %. In terms of lower limits, the acetone concentration in the lights removal distillate stream can be greater than 0.35 wt %, e.g., greater than 0.48 wt %, greater than 0.66 wt %, greater than 0.91 wt %, greater than 1.3 wt %, greater than 1.7 wt %, greater than 2.4 wt %, greater than 3.3 wt %, greater than 4.5 wt %, or greater than 6.2 wt %.

This column operates under slightly above atmospheric pressure and contains 46 theoretical stages. In some embodiments, the lights removal distillation column is operated at a pressure ranging from 50 kPa to 250 kPa, e.g., from 50 kPa to 225 kPa, from 60 kPa to 215 kPa, from 60 kPa to 195 kPa, from 60 kPa to 140 kPa, from 75 kPa to 120 kPa, from 80 kPa to 100 kPa, or from 85 kPa to 95. In terms of upper limits, the lights removal distillation column operating pressure can be less than 250 kPa, e.g., less than 225 kPa, less than 215 kPa, less than 200 kPa, less than 195 kPa, less than 175 kPa, less than 140 kPa, less than 120 kPa, less than 100 kPa, or less than 95 kPa. In terms of lower limits, the lights removal distillation column operating pressure can be greater than 50 kPa, e.g., greater than 60 kPa, greater than 75 kPa, greater than 80 kPa, or greater than 85 kPa. Operation at these pressures, in some cases, provides for the aforementioned benefits.

The structure of the lights removal distillation column (and the columns generally) can vary widely according to designs known to those of ordinary skill in the art, and any suitable column can be employed as long as the separation specifications described herein are achieved. For example, the lights removal distillation column can include any suitable separation device or combination of separation devices. The lights removal distillation column can include a column, e.g., a standard distillation column, an extractive distillation column and/or an azeotropic distillation column. In some cases, the term "lights removal distillation column" refers to multiple distillation columns configured to operate in conjunction with one another. In some cases, one or more of the aforementioned columns, e.g., the lights column, may beneficially comprise trays comprising or made of zirconium, or stainless steel, or combinations thereof.

Due to potential for fouling in the upper stages, this column may be designed with fouling resistant trays as internals in rectifying section. This column may be equipped with a forced circulation reboiler and a shell and tube overhead condenser with a reflux drum.

Extraction/Caustic Treatment

As noted above, the process employs an extraction step, e.g., a liquid-liquid extraction (LLE), that also employs a caustic treatment. During the extraction step, the distillation bottoms stream is extracted in an extraction (third) column (along with the caustic treatment) to yield a raffinate stream comprising acetonitrile (at least a portion of the acetonitrile from distillation bottoms stream) and low amounts of acrylonitrile, e.g., less than 200 ppm, less than 100 ppm, or less than 25 ppm, and an extract stream comprising water and acrylonitrile. Beneficially, the disclosed processes achieve the caustic reaction of the acrylonitrile as well as the extraction of the other aforementioned impurities in a single extraction step. Thus, the disclosed process advantageously reduces the number of units necessary to achieve suitable separations, which contributes to a significant reduction in, inter alia, capital expenditure. In some cases, the caustic treatment yields a cyanide-containing product, e.g., a metal cyanide, e.g., sodium cyanide, formed from the reaction of the caustic and the hydrogen cyanide.

The inventors have found that, in some cases, an accelerator, e.g., methanol, may be employed to improve the extraction step. The accelerator may be utilized during the extraction/caustic treatment. In some embodiments, the accelerator may be employed at positions upstream of the extraction/caustic treatment. In some cases, the accelerator may be added to the distillation column, e.g., the distillation bottoms stream, before or while the bottoms stream is provided to the column. In some cases, the accelerator may be provided directly to the (extraction) column. In some embodiments, the accelerator may be employed at positions upstream of the extraction/caustic treatment. In such cases, the resultant feed to the extraction column may comprise the accelerator in the amounts mentioned below.

The accelerator may vary widely. In some cases, the accelerator may comprise alcohols (diols), ethers, (small alkyl) acids, aldehydes, amines, or esters, or combinations thereof. In some cases, the accelerator may comprise ethanol, 1-propanol, 2-propanol, t-butanol, 1-hexanol, ethylene glycol, propylene glycol, glycerine, cyclohexanol, triethylamine, xylitol, ethanolamine, diethanolamine, morpholine, triethanolamine, or piperidine, or combinations thereof. In some cases, the accelerator may comprise an alcohol, e.g., methanol. In some embodiments, the accelerator is a compound that is soluble in both the caustic and in acetonitrile.

The LLE column, in some cases, is fed with a concentrated aqueous alkali solution, e.g., a caustic solution. For example, the extraction solvent may comprise a basic solvent, e.g., sodium hydroxide and/or potassium hydroxide. This listing is not exhaustive and other caustics are contemplated. As one example a greater than 10% caustic solution, e.g., sodium hydroxide solution, is employed, e.g., greater than 15% greater than 20%, greater than 25%, or greater than 30%. The caustic is combined with the distillate and extracted, e.g., in a countercurrent manner. The raffinate (organic liquid phase) and the extract (aqueous liquid phase) result therefrom.

Without being bound by theory, it is believed that the caustic solution advantageously serves the purpose of promoting the extraction of water from the feed and/or enabling the base catalyzed hydrolysis of acrylonitrile.

The inventors have found that the liquid-liquid extraction/caustic process is particularly efficient for the specific streams that contain impurities such as hydrogen cyanide and acrylonitrile (in addition to water), e.g., the distillate bottoms. Without being bound by theory, it is postulated that these impurities may react, e.g., hydrolyze, with the concentrated alkali solution to form compounds with low volatility, which in turn facilitates the separation from the desired acetonitrile.

In some embodiments, the extraction/caustic treatment beneficially helps to break the acetonitrile/water azeotrope compositions that may have formed in the various streams, e.g., the distillate bottoms. The dehydrated acetonitrile in the raffinate is withdrawn from the top of the extraction column, and the aqueous alkali solution, diluted with the extracted water, is withdrawn from the bottom of the extraction column.

In some embodiments, the feed stream to the extraction column, e.g., the distillate bottoms stream comprises accelerator. In some cases, the methanol is present in specific amounts. The concentration of methanol in the bottoms stream can range, for example, from 0.1 wt % to 20 wt %, e.g., from 0.5 wt % to 15 wt %, from 1 wt % to 15 wt %, from 1 wt % to 10 wt %, from 2 wt % to 8 wt %, or from 3 wt % to 7 wt %. In terms of upper limits, the accelerator concentration in the bottoms stream can be less than 20 wt %, e.g., less than 15 wt %, less than 12 wt %, less than 10 wt %, less than 9 wt %, less than 8 wt %, less than 7 wt %, or less than 6 wt %. In terms of lower limits, the accelerator concentration in the bottoms stream can be greater than 0.1 wt %, e.g., greater than 0.2 wt %, greater than 0.5 wt %, greater than 0.7 wt %, greater than 1 wt %, greater than 1.5 wt %, greater than 2 wt %, greater than 2.5 wt %, greater than 3 wt %, or greater than 3.5 wt %.

The concentration of acrylonitrile in the raffinate is particularly low. For example, in some embodiments, the concentration of acrylonitrile in the raffinate ranges from 0 ppb to 200 ppm, e.g., from 1 ppb to 100 ppm, from 10 ppb to 50 ppm, from 10 ppb to 25 ppm, or from 10 ppb to 22 ppm. In terms of upper limits, the acrylonitrile concentration in the raffinate can be less than 200 ppm e.g., less than 100 ppm, less than 50 ppm, less than 35 ppm, less than 25 ppm, less than 22 ppm, less than 10 ppm, less than 1 ppm, less than 100 ppb, or less than 10 ppb. In terms of lower limits, the acrylonitrile concentration in the raffinate can be 0 ppb, e.g., greater than 1 ppb, greater than 10 ppb, greater than 100 ppb, or greater than 1 ppm. In some cases, the raffinate comprises little or even no acrylonitrile.

The raffinate may also comprise hydrogen cyanide in low amounts, if any. The ranges and limits discussed above for acrylonitrile are applicable to hydrogen cyanide as well. Because hydrogen cyanide is effectively separated as disclosed, digestion units are not necessary to achieve suitable hydrogen cyanide removal.

These low levels of acrylonitrile have been found to enable the provide for unexpected downstream separation efficiencies, e.g., wherein the final product comprises less than 50 ppm acrylonitrile, e.g., less than 25 ppm, less than 10 ppm, less than 1 ppm, less than 100 ppb, or less than 50 ppb.

Advantageously, the acetonitrile content in the raffinate is surprisingly pure. In some embodiments, the concentration of acetonitrile in the raffinate ranges from 25 wt % to 95 wt %, e.g., from 30 wt % to 90 wt %, from 40 wt % to 85 wt %, from 50 wt % to 85 wt %, from 60 wt % to 85 wt %, or from 65 wt % to 85 wt %. In terms of upper limits, the acetonitrile concentration in the raffinate can be less than 95 wt %. e.g., less than 90 wt %, less than 85 wt %, less than 82 wt %, less than 80 wt %, or less than 78 wt %. In terms of lower limits, the acetonitrile concentration in the raffinate can be greater than 25 wt %, e.g., greater than 30 wt %, greater than 40 wt %, greater than 50 wt %, greater than 60 wt %, greater than 70 wt %, greater than 72 wt %.

The raffinate also comprises low amounts of water. In some embodiments, the concentration of water in the raffinate ranges from 0 wt % to 50 wt %, e.g., from 0 wt % to 25 wt %, from 1 wt % to 30 wt %, from 2 wt % to 25 wt %, from 5 wt % to 25 wt %, 5 wt % to 20 wt %, or from 10 wt % to 20 wt %. In terms of upper limits, the water concentration in the raffinate can be less than 50 wt %, e.g., less than 40 wt %, less than 30 wt %, less than 25 wt %, less than 20 wt %, or less than 15 wt %. In terms of lower limits, the water concentration in the raffinate can be greater than 0, e.g., greater than 0.1 wt %, greater than 1 wt %, greater than 2 wt %, greater than 5 wt %, greater than 10 wt %, or greater than 12 wt %.

The raffinate may also comprise azeotrope compositions, e.g., acrylonitrile-water or acetonitrile-water azeotrope compositions.

In some embodiments, the raffinate comprises accelerator. In some cases, the accelerator is present in specific amounts. The concentration of methanol in the raffinate stream can range, for example, from 0.1 wt % to 20 wt %, e.g., from 0.5 wt % to 15 wt %, from 1 wt % to 15 wt %, from 1 wt % to 10 wt %, from 2 wt % to 8 wt %, or from 3 wt % to 7 wt %. In terms of upper limits, the accelerator concentration in the raffinate can be less than 20 wt %, e.g., less than 15 wt %, less than 12 wt %, less than 10 wt %, less than 9 wt %, less than 8 wt %, less than 7 wt %, or less than 6 wt %. In terms of lower limits, the accelerator concentration in the raffinate can be greater than 0.1 wt %, e.g., greater than 0.2 wt %, greater than 0.5 wt %, greater than 0.7 wt %, greater than 1 wt %, greater than 1.5 wt %, greater than 2 wt %, greater than 2.5 wt %, greater than 3 wt %, or greater than 3.5 wt %.

The resultant extract comprises other impurities such as caustic reaction products, e.g., metal cyanides, e.g., sodium cyanide. The lower volatility compounds (caustic reaction products) may be present in the extract stream in an amount ranging from 0.0001 wt % to 5.0 wt %, e.g., from 0.05 wt % to 3.0 wt %, from 0.05 wt % to 2.0 wt %, from 0.07 wt % to 2.0 wt %, from 0.07 wt % to 1.5 wt %, from 0.1 wt % to 1 wt %, or from 0.1 wt % to 0.7 wt %. In terms of upper limits, the lower volatility compound concentration in the extract stream can be less than 5.0 wt %, e.g., less than 3.0 wt %, less than 2.0 wt %, less than 1.5 wt %, less than 1.0 wt %, less than 0.7 wt %, less than 0.5 wt %, less than 0.1 wt %, less than 750 ppm, less than 500 ppm, less than 250 ppm, less than 200 ppm, or less than 100 ppm. In terms of lower limits, the lower volatility compound concentration in the extract stream can be greater than 0.01 wt %, e.g., greater than 0.05 wt %, greater than 0.07 wt %, greater than 0.1 wt %, or greater than 0.15 wt %. As one example, some acrylonitrile may be reacted to form hydroxypropionitrile and the hydroxypropionitrile may be present in these amounts.

In some embodiments, the concentration of water in the extract stream ranges from 30 wt % to 95 wt %, e.g., from 40 wt % to 92 wt %, from 50 wt % to 90 wt %, from 70 wt % to 90 wt %, or from 75 wt % to 85 wt %. In terms of upper limits, the water concentration in the extract stream can be less than 95 wt %, e.g., less than 92 wt %, less than 90 wt %, or less than 85 wt %. In terms of lower limits, the water concentration in the extract stream can be greater than 30 wt %, e.g., greater than 40 wt %, greater than 50 wt %, greater than 60 wt %, greater than 70 wt %, greater than 75 wt %, or greater than 80 wt %.

In some cases caustic is present in the extract as well.

In some embodiments, the mass ratio of the water in the extract stream to the water in the raffinate stream ranges from 40:1 to 900:1, e.g., from 40:1 to 260:1, from 55:1 to 350:1, from 75:1 to 480:1, from 100:1 to 660:1, or from 140:1 to 900:1. In terms of upper limits, the mass ratio of water in the extract stream to the raffinate stream can be less than 900:1, e.g., less than 660:1, less than 480:1, less than 350:1, less than 260:1, less than 190:1, less than 140:1, less than 100:1, less than 75:1, or less than 55:1. In terms of lower limits, the mass ratio of water in the extract stream to the raffinate stream can be greater than 40:1, e.g., greater than 55:1, greater than 75:1, greater than 100:1, greater than 140:1, greater than 190:1, greater than 260:1, greater than 350:1, greater than 480:1, or greater than 660:1.

In some embodiments, the concentration of allyl alcohol in the raffinate stream ranges from 0 wt % to 8 wt %, e.g., from 0 wt % to 1.3 wt %, from 0.13 wt % to 1 wt %, from 0.2 wt % to 3.2 wt %, from 0.32 wt % to 5 wt %, or from 0.5 wt % to 8 wt %. In terms of upper limits, the allyl alcohol concentration in the raffinate stream can be less than 8 wt %, e.g., less than 5 wt %, less than 3.2 wt %, less than 2 wt %, less than 1.3 wt %, less than 0.8 wt %, less than 0.5 wt %, less than 0.3 wt %, less than 0.2 wt %, or less than 0.13 wt %. In terms of lower limits, the allyl alcohol concentration in the raffinate stream can be greater than 0.08 wt %, e.g., greater than 0.13 wt %, greater than 0.2 wt %, greater than 0.3 wt %, greater than 0.5 wt %, greater than 0.8 wt %, greater than 1.3 wt %, greater than 2 wt %, greater than 3.2 wt %, or greater than 5 wt %. Similar amounts of oxazole may also be present.

In some embodiments, the mass ratio of the acetonitrile to the water in the raffinate stream ranges from 60:1 to 5000:1, e.g., from 60:1 to 850:1, from 93:1 to 1300:1, from 150:1 to 2100:1, from 230:1 to 3200:1, or from 350:1 to 5000:1. In terms of upper limits, the mass ratio of acetonitrile to water in the raffinate stream can be less than 5000:1, e.g., less than 3200:1, less than 2100:1, less than 1300:1, less than 850:1, less than 550:1, less than 350:1, less than 230:1, less than 150:1, or less than 93:1. In terms of lower limits, the mass ratio of acetonitrile to water in the raffinate stream can be greater than 60:1, e.g., greater than 93:1, greater than 150:1, greater than 23-:1, greater than 350:1, greater than 550:1, greater than 850:1, greater than 1300:1, greater than 2100:1, or greater than 3200:1.

Purification (Drying and/or Heavies Removal)

The provided separation process further includes one or more purification unit operations to remove remaining trace impurities and/or water.

In some cases, a drying step is employed following the extraction/caustic treatment. In some cases, a heavy removal step is employed. For example, the feed to the heavy ends column may be separated into a distillate comprising a (high purity) product acetonitrile stream and a bottoms heavies stream.

The concentration of acetonitrile in the product acetonitrile stream can range, for example, from 98 wt % to 100 wt %, e.g., from 98 wt % to 99.999 wt %, from 98 wt % to 99.92 wt %, from 98.82 wt % to 99.95 wt %, from 99.31 wt % to 99.97 wt %, from 99.59 wt % to 99.98 wt %, or from 99.76 wt % to 99.99 wt %. In terms of lower limits, the acetonitrile concentration in the product acetonitrile stream can be greater than 98 wt %, e.g., greater than 98.83 wt %, greater than 99.31 wt %, greater than 99.59 wt %, greater than 99.76 wt %, greater than 99.86 wt %, greater than 99.92 wt %, greater than 99.95 wt %, greater than 99.97 wt %, greater than 99.98 wt %, or greater than 99.99 wt %.

The concentration of acetonitrile in the bottoms heavies stream can range, for example, from 3.5 wt % to 45 wt %, e.g., from 3.5 wt % to 16 wt %, from 4.5 wt % to 21 wt %, from 5.8 wt % to 27 wt %, from 7.5 wt % to 35 wt %, or from 9.7 wt % to 34 wt %. In terms of upper limits, the acetonitrile concentration in the heavies bottoms stream can be less than 45 wt %, e.g., less than 35 wt %, less than 27 wt %, less than 21 wt %, less than 16 wt %, less than 13 wt %, less than 9.7 wt %, less than 7.5 wt %, less than 5.8 wt %, or less than 4.5 wt %. In terms of lower limits, the acetonitrile concentration in the heavies bottoms stream can be greater than 3.5 wt %, e.g., greater than 4.5 wt %, greater than 5.8 wt %, greater than 7.5 wt %, greater than 9.7 wt %, greater than 13 wt %, greater than 16 wt %, greater than 21 wt %, greater than 27 wt %, or greater than 35 wt %.

In some embodiments, the concentration of heavies in the bottoms stream ranges from 40 wt % to 98 wt %, e.g., from 40 wt % to 95 wt %, from 45 wt % to 90 wt %, from 55 wt % to 85 wt %, from 60 wt % to 80 wt %, or from 65 wt % to 75 wt %. In terms of upper limits, the heavies concentration in the bottoms stream can be less than 98 wt %, e.g., less than 95 wt %, less than 90 wt %, less than 85 wt %, less than 80 wt %, less than 75 wt %, or less than 72 wt %. In terms of lower limits, the heavies concentration in the bottoms stream can be greater than 40 wt %, e.g., greater than 45 wt %, greater than 50 wt %, greater than 55 wt %, greater than 60 wt %, greater than 65 wt %, or greater than 68 wt %.

The mass ratio of the acetonitrile in the product acetonitrile stream to the acetonitrile in the heavies removal bottoms stream can range, for example, from 4.5:1 to 90:1, e.g., from 4.5:1 to 27:1, from 6.1:1 to 37:1, from 8.2:1 to 49:1, from 11:1 to 67:1, or from 15:1 to 90:1. In terms of upper limits, the mass ratio of acetonitrile in the product acetonitrile stream to the heavies removal bottom stream can be less than 90:1, e.g., less than 67:1, less than 49:1, less than 37:1, less than 27:1, less than 20:1, less than 15:1, less than 11:1, less than 8:1, or less than 6.1:1. In terms or lower limits, the mass ratio of acetonitrile in the product acetonitrile stream to the heavies removal bottoms stream can be greater than 4.5:1, e.g., greater than 6.1:1, greater than 8.2:1, greater than 11:1, greater than 15:1, greater than 20:1, greater than 27:1, greater than 37:1, greater than 49:1, or greater than 67:1.

The concentration of propionitrile in the heavies bottoms stream can range, for example, from 2 wt % to 35 wt %, e.g., from 2 wt % to 11 wt %, from 2.7 wt % to 15 wt %, from 3.5 wt % to 20 wt %, from 4.7 wt % to 26 wt %, or from 6.3 wt % to 35 wt %. In terms of upper limits, the propionitrile concentration in the heavies bottoms stream can be less than 35 wt %, e.g., less than 26 wt %, less than 20 wt %, less than 15 wt %, less than 11 wt %, less than 8.4 wt %, less than 6.3 wt %, less than 4.7 wt %, less than 3.5 wt %, or less than 2.7 wt %. In terms of lower limits, the propionitrile concentration in the heavies bottoms stream can be greater than 2 wt %, e.g., greater than 2.7 wt %, greater than 3.5 wt %, greater than 4.7 wt %, greater than 6.3 wt %, greater than 8.4 wt %, greater than 11 wt %, greater than 15 wt %, greater than 20 wt %, or greater than 26 wt %.

In some embodiments, the concentration of allyl alcohol in the heavies bottoms stream ranges from 0.75 ppm to 20 ppm, e.g., from 0.75 ppm to 5.4 ppm, from 1 ppm to 7.5 ppm, from 1.4 ppm to 10 ppm, from 2 ppm to 14 ppm, or from 2.8 ppm to 20 ppm. In terms of upper limits, the allyl alcohol concentration in the heavies bottoms stream can be less than 20 ppm, e.g., less than 14 ppm, less than 10 ppm, less than 7.5 ppm, less than 5.4 ppm, less than 3.9 ppm, less than 2.8 ppm, less than 2 ppm, less than 1.4 ppm, or less than 1 ppm. In terms of lower limits, the allyl alcohol concentration in the heavies bottoms stream can be greater than 0.75 ppm, e.g., greater than 1 ppm, greater than 1.4 ppm, greater than 2 ppm, greater than 2.8 ppm, greater than 3.9 ppm, greater than 5.4 ppm, greater than 7.5 ppm, greater than 10 ppm, or greater than 14 ppm.

The disclosed separation schemes, e.g., the final purification steps provide for unexpected separation efficiency with regard to amines.

In some embodiments, any or some of the components/steps/operations disclosed herein may be considered optional. In some cases, the disclosed process may expressly exclude any or some of the aforementioned components/steps/operations in this description, e.g., via claim language. For example, claim language may be modified to recite that the disclosed processes do not utilize or comprise one or more of the aforementioned steps, e.g., the disclosed process do not employ a finishing step and/or a (hydrogen cyanide/acrylonitrile) digestion step.

As used herein, "greater than" and "less than" limits may also include the number associated therewith. Stated another way, "greater than" and "less than" may be interpreted as "greater than or equal to" and "less than or equal to." It is contemplated that this language may be subsequently modified in the claims to include "or equal to." For example, "greater than 4.0" may be interpreted as, and subsequently modified in the claims as "greater than or equal to 4.0."

EXAMPLES

The FIGURE illustrates an exemplary separation scheme 100. As shown in the scheme, feedstock stream 103 is fed to dehydration distillation column 104. The composition of the feedstock stream 103 includes 15.8 wt % acetonitrile, 5.2 wt % methanol, 0.9 wt % hydrogen cyanide, 71.1% water, 0.4 wt % allyl alcohol, 0.7 wt % oxazole, 0.4 wt % propionitrile, 0.4 wt % acrylonitrile, 0.1 wt % acetone, 3.2 wt % heavies, and about 2 wt % other impurities (including cis-crotonitrile, trans-crotonitrile, fumaronitrile, succinonitrile, acrylamide, acrolein cyanohydrin, maleonitrile, and mixtures thereof).

Distillation of feedstock stream 103 in dehydration distillation column 104 yields dehydrated acetonitrile stream 106 and dehydration bottoms stream 105. Distillation column 104 has 37 stages and operates with a reflux ratio of 0.4. Distillation column 104 operates with a top pressure of 33 kPa and a bottom pressure of 34.5 kPa. The temperature at the top of the distillation column 104 is 46.8° C. and the temperature at the bottom of the distillation column 104 is 72.6° C.

Dehydrated acetonitrile stream 106 recovers more than 91% of the acetonitrile with a relatively low amount of water (less than 5%) from the feedstock stream 103. The composition of dehydrated acetonitrile stream 106 includes acetonitrile, methanol, water, allyl alcohol, oxazole, propionitrile, acrylonitrile, and acetone from the feedstock stream. Due to the operation of the dehydration distillation column 104 the allyl alcohol in dehydrated acetonitrile stream 106 is less than 0.1 ppm. The composition of the dehydrated acetonitrile stream 106 includes 74.6 wt % acetonitrile, 1.8 wt % methanol, 2.0 wt % hydrogen cyanide, 13.6% water, 1.9 wt % oxazole, 0.8 wt % propionitrile, 0.8 wt % acrylonitrile, 0.1 wt % acetone, 3.2 wt % heavies, and about 1.1 wt % other impurities (including cis-crotonitrile, trans-crotonitrile, fumaronitrile, succinonitrile, acrylamide, acrolein cyanohydrin, maleonitrile, and mixtures thereof).

Dehydration distillation column 104 operates to remove methanol in the bottoms stream 105. Under these conditions, more than 75% of the methanol from the feedstock stream 103 is retained in the bottoms stream 105. The composition of dehydration bottoms stream 105 includes water, methanol, and allyl alcohol from the feedstock stream. The composition of the dehydration bottoms stream 105 includes 92.3 wt % water, 3.9 wt % methanol, 0.4 wt % acetonitrile, 0.3 wt % allyl alcohol, 1.5 wt % heavies, and about 1.5 wt % other impurities (including acrylonitrile, oxazole, propionitrile, acetone, cis-crotonitrile, trans-crotonitrile, fumaronitrile, succinonitrile, acrylamide, acrolein cyanohydrin, maleonitrile, and mixtures thereof).

Dehydrated acetonitrile stream 106 is fed to lights removal column 107. Lights removal column 107 has 45 stages and operates with a reflux ratio of 25. Lights removal column 107 operates with a top pressure of 115.1 kPa and a bottom pressure of 117.2 kPa. The temperature at the top of the column 107 is 64.6° C. and the temperature at the bottom of the column 107 is 89° C. Lights removal column 107 yields lights distillate 108 and lights bottoms stream 109 that recovers 94% of the acetonitrile. The lights bottoms stream 109 contains very low amounts of acrylonitrile (600 ppm by weight or less). Methanol and oxazole are collected in the lights distillate 108. The composition of lights bottoms stream 109 includes 79.5 wt % acetonitrile, 14.4 wt % water, 0.5 wt % oxazole, 0.9 wt % propionitrile, 0.1 wt % acrylonitrile, 3.5 wt % heavies, and about 1.2 wt % other impurities (including cis-crotonitrile, trans-crotonitrile, fumaronitrile, succinonitrile, acrylamide, acrolein cyanohydrin, maleonitrile, and mixtures thereof).

Lights bottoms stream 109 is fed to extractor 110. Extraction of lights bottoms stream 109 in extractor 110 yields raffinate stream 111 comprising acetonitrile and low amounts of acrylonitrile and extract stream 112 comprising water, hydroxypropionitrile, and acrylonitrile. Acrylonitrile reacts via caustic hydrolysis to form hydroxypropionitrile. Accelerator, in particular methanol, is fed to extractor via accelerator feed 113. Caustic is fed to extractor 110 via caustic feed 114, which comprises 75 wt % water and 25 wt % sodium hydroxide. The accelerator may also be employed at other positions upstream of the extraction/caustic treatment.

The raffinate stream 111 includes 81.7 wt % acetonitrile, 12.1 wt % water, 0.5 wt % oxazole, 0.9 wt % propionitrile, 3.5 wt % heavies, and about 1.2 wt % other impurities (including cis-crotonitrile, trans-crotonitrile, fumaronitrile, succinonitrile, acrylamide, acrolein cyanohydrin, maleonitrile, and mixtures thereof).

Raffinate stream 111 is further purified, e.g., dried and finished. Raffinate stream 111 is fed to drying column 115, which yields drying distillate 116 and drying bottoms 117. Drying column 115 has 45 stages and operates with a reflux ratio of 1.5. Drying column 115 operates with a top pressure of 194.4 kPa and a bottom pressure of 195.5 kPa. The temperature at the top of the distillation column 104 is 96.3° C. and the temperature at the bottom of the drying column 115 is 106.2° C.

Drying distillate 116 is returned to column 104. Any amount of acetonitrile in the drying distillate 116 is returned to be further recovered. The drying distillate 111 includes 78.3 wt % acetonitrile, 20.5 wt % water, 0.9 wt % oxazole, 0.1 wt % propionitrile, and about 0.2 wt % cis-crotonitrile.

The drying bottoms 117 is enriched in acetonitrile and contains low amounts of water (<75 ppm by weight), acrylonitrile (<0.4 ppm by weight), and oxazole (<0.1 ppm by weight). The drying bottoms 117 includes 86.6 wt % acetonitrile, 2.0 wt % propionitrile, 8.6 wt % heavies and about 2.7 wt % cis-crotonitrile.

Drying bottoms 117 is fed to product column (heavies column) 118, which yields high purity acetonitrile 119 and bottoms (heavies) stream 120. Heavies column 118 has 33 stages and operates with a reflux ratio of 2.6. Heavies column 118 operates with a top pressure of 26.2 kPa and a bottom pressure of 30.3 kPa. The temperature at the top of the distillation column 118 is 45.2° C. and the temperature at the bottom of the drying column 118 is 62.2° C. The process recovers a product stream in the high purity acetonitrile 119 that is greater than 99.99 wt % acetonitrile.

The heavies stream 120 contains 58.0 wt % heavies, 18 wt % cis-crotonitrile, 10.5 wt % acetonitrile, and 13.5 wt % propionitrile.

EMBODIMENTS

The following embodiments are contemplated. All combinations of features and embodiments are contemplated.

Embodiment 1: A process for producing acetonitrile, the process comprising dehydrating a feedstock stream comprising acetonitrile, acrylonitrile, allyl alcohol, and water, and optionally methanol, in a dehydration (first) column to yield a dehydrated acetonitrile stream comprising acetonitrile and acrylonitrile, less than 1 wt % allyl alcohol, and less than 50 wt % water, and optionally hydrogen cyanide; distilling the dehydrated acetonitrile stream in a lights (second) column to yield a distillate stream comprising lights, and a bottoms stream comprising acetonitrile, acrylonitrile, water, and optionally hydrogen cyanide and acrylonitrile; extracting the distillation bottoms stream in an extraction (third) column to yield a raffinate stream comprising acetonitrile and less than 200 ppm acrylonitrile and or less than 1 wt % metal cyanide, and an extract stream comprising water and acrylonitrile; purifying the raffinate stream to yield a product acetonitrile stream.

Embodiment 2: An embodiment of embodiment 1, wherein the dehydration is conducted at a pressure less than 150 kPa.

Embodiment 3: An embodiment of embodiment 1 or 2, wherein an accelerator is utilized during the extracting.

Embodiment 4: An embodiment of any of the embodiments of embodiment 1-3, wherein the bottoms stream comprises from 0.1 wt % to 20 wt % methanol.

Embodiment 5: An embodiment of any of the embodiments of embodiment 1-4, wherein the raffinate stream comprises less than 25 ppm acrylonitrile.

Embodiment 6: An embodiment of any of the embodiments of embodiment 1-5, wherein the raffinate stream comprises less than 200 ppm hydrogen cyanide and less than 50 wt % water.

Embodiment 7: An embodiment of any of the embodiments of embodiment 1-6, wherein the dehydration yields a water stream comprising water, allyl alcohol, methanol, and heavies.

Embodiment 8: An embodiment of any of the embodiments of embodiment 1-7, wherein the dehydrated acetonitrile stream comprises less than 20 wt % polymerized HCN.

Embodiment 9: An embodiment of any of the embodiments of embodiment 1-8, wherein the dehydrated acetonitrile stream comprises less than 25 wt % heavies.

Embodiment 10: An embodiment of any of the embodiments of embodiment 1-9, wherein the lights distillate stream comprises oxazole, methanol, and/or acrylonitrile.

Embodiment 11: An embodiment of any of the embodiments of embodiment 1-10, wherein lights bottoms stream further comprises acetonitrile-water azeotrope composition.

Embodiment 12: An embodiment of any of the embodiments of embodiment 1-11, wherein the extraction is conducted counter currently.

Embodiment 13: An embodiment of any of the embodiments of embodiment 1-12, wherein the raffinate stream comprises less than 25 wt % water and less than 50 ppm acrylonitrile.

Embodiment 14: An embodiment of any of the embodiments of embodiment 1-13, wherein the purifying comprises distilling the raffinate stream in a drying (fourth) column to yield an overhead comprising acetonitrile-water azeotrope and a bottoms stream comprising acetonitrile and low amounts of water.

Embodiment 15: An embodiment of any of the embodiments of embodiment 1-14, further comprising recycling the drying column overhead to the dehydration column.

Embodiment 16: An embodiment of any of the embodiments of embodiment 1-15, wherein the purifying further comprises distilling the drying column bottoms in a product (fifth) column to yield a product stream comprising high purity acetonitrile.

Embodiment 17: An embodiment of any of the embodiments of embodiment 1-16, wherein the drying columns bottom comprises propionitrile and less than 5 wt % water and wherein the distilling in the product column yields an overhead comprising greater than 95 wt % acetonitrile and a bottoms comprising propionitrile and optionally heavies.

While the disclosure has been described in detail, modifications within the spirit and scope of the disclosure will be readily apparent to those of skill in the art in view of the foregoing discussion, relevant knowledge in the art, and references discussed above in connection with the Background and Detailed Description, the disclosures of which are all incorporated herein by reference. In addition, it should be understood that aspects of the disclosure and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetonitrile, the process comprising:

dehydrating a feedstock stream comprising acetonitrile, acrylonitrile, allyl alcohol, and water in a dehydration (first) column to yield a dehydrated acetonitrile stream comprising acetonitrile and acrylonitrile, less than 1 wt % allyl alcohol, and less than 50 wt % water, and optionally hydrogen cyanide;

distilling the dehydrated acetonitrile stream in a lights (second) column to yield a lights distillate stream comprising lights, and a bottoms stream comprising acetonitrile, water, and optionally hydrogen cyanide and acrylonitrile;

extracting the bottoms stream in an extraction (third) column to yield a raffinate stream comprising acetonitrile and less than 200 ppm acrylonitrile and an extract stream comprising water and acrylonitrile; and purifying the raffinate stream to yield a product acetonitrile stream.

2. The process of claim 1, wherein the dehydration is conducted at a pressure less than 150 kPa.

3. The process of claim 1, wherein the feedstock stream comprises methanol.

4. The process of claim 1, wherein an accelerator is utilized during the extracting.

5. The process of claim 1, wherein the bottoms stream comprises from 0.1 wt % to 20 wt % methanol.

6. The process of claim 1, wherein the raffinate stream comprises less than 25 ppm acrylonitrile.

7. The process of claim 1, wherein the raffinate stream comprises less than 200 ppm hydrogen cyanide and less than 50 wt % water.

8. The process of claim 1, wherein the raffinate stream comprises less than 1 wt % metal cyanide.

9. The process of claim 1, wherein the dehydration yields a water stream comprising water, allyl alcohol, methanol, and heavies.

10. The process of claim 1, wherein the dehydrated acetonitrile stream comprises less than 20 wt % polymerized HCN.

11. The process of claim 1, wherein the dehydrated acetonitrile stream comprises less than 25 wt % heavies.

12. The process of claim 1, wherein the lights distillate stream comprises oxazole, methanol, and/or acrylonitrile.

13. The process of claim 1, wherein lights bottoms stream further comprises acetonitrile-water azeotrope composition.

14. The process of claim 1, wherein the extraction is conducted countercurrently.

15. The process of claim 1, wherein the raffinate stream comprises less than 25 wt % water and less than 50 ppm acrylonitrile.

16. The process of claim 1, wherein the purifying comprises distilling the raffinate stream in a drying (fourth) column to yield an overhead stream comprising acetonitrile-water azeotrope and a second bottoms stream comprising acetonitrile and less than 75 ppm water.

17. The process of claim 16, further comprising recycling the overhead stream to the dehydration column.

18. The process of claim 16, wherein the purifying further comprises distilling the second bottoms stream in a product (fifth) column to yield the product acetonitrile stream comprising greater than 99.99 wt % acetonitrile.

19. The process of claim 18, wherein the second bottoms stream comprises propionitrile and less than 5 wt % water and wherein the distilling in the product column yields the product acetonitrile stream as a second overhead stream and a third bottoms stream comprising propionitrile and optionally heavies.

20. The process of claim 1, wherein the dehydration is conducted at a pressure less than 100 kPa.

* * * * *